US 7,842,015 B2

(12) United States Patent
Chachques et al.

(10) Patent No.: US 7,842,015 B2
(45) Date of Patent: Nov. 30, 2010

(54) DIAGNOSTIC AND INJECTION CATHETER, IN PARTICULAR FOR AN APPLICATION IN CARDIOLOGY

(76) Inventors: Juan Carlos Chachques, 116 Rue de la Tour, Paris (FR) 75116; Jesus Herreros, Paseo Sarasate 20, Pamplona (ES) 31001; Ignacio Vega Quilez, General Eguia 48, Bilbao-Vizcaya (ES) 48013

( * ) Notice: Subject to any disclaimer, the term of this patent is extended or adjusted under 35 U.S.C. 154(b) by 1763 days.

(21) Appl. No.: 10/995,160

(22) Filed: Nov. 24, 2004

(65) Prior Publication Data

US 2005/0113760 A1     May 26, 2005

(30) Foreign Application Priority Data

Nov. 24, 2003   (FR)   .................................. 03 13719

(51) Int. Cl.
    *A61M 25/02*   (2006.01)
(52) U.S. Cl. ........................ 604/174; 607/126
(58) Field of Classification Search ................ 604/174, 604/164.01, 164.03, 164.04, 176; 607/126, 607/116, 119
    See application file for complete search history.

(56) References Cited

U.S. PATENT DOCUMENTS

| | | | | |
|---|---|---|---|---|
| 5,336,252 | A | * | 8/1994 | Cohen ........................ 607/119 |
| 5,904,711 | A | * | 5/1999 | Flom et al. ................... 607/129 |
| 6,056,743 | A | | 5/2000 | Ellis et al. |
| 6,143,019 | A | | 11/2000 | Motamedi et al. |
| 2002/0029037 | A1 | | 3/2002 | Kim |
| 2002/0095124 | A1 | | 7/2002 | Palasis et al. |

FOREIGN PATENT DOCUMENTS

| | | |
|---|---|---|
| EP | 0876803 A2 | 11/1998 |
| EP | 0876803 A3 | 4/1999 |
| WO | WO 99/39624 | 8/1999 |
| WO | WO 03/090636 | 11/2003 |

OTHER PUBLICATIONS

The Society of Thoracic Surgeons, Cellular Cardiomyoplasty: Clinical Application, Juan C. Chachques, MD, PhD, Christophe Acar, Md, Jesus Herreros, MD, Jorge C. Trainini, MD, Felipe Prosper, MD, Nicola D'Attelis, MD, Jean-Noel Fabiani, MD, and Alain F. Carpentier, MD, PhD, (Ann Thorac Surg 2004;77:1121-30).

European Surgery, Main Topics: Surgery in End-stage Cardiac Disease, J.C. Chachques, O. Schussler, R. Giambroni, J. Tommasi, J.-N. Fabiani and A. Carpentier, Eur Surg (2004) 36/4: 217-221.

The Journal of Thoracic and Cardiovascular Surgery, Angiogenic growth factors and/or cellular therapy for myocardial regeneration: A comparative study, Juan C. Chachques, MD, PhD, Fabricio Duarte, MD, Barbara Cattadori, MD, Abdel Shafy, MD, Nermine Lila, DVM, PhD, Gilles Chatellier, MD, Jean-Noel Fabiani, MD, and Alain F. Carpentier, MD, PhD, vol. 128, No. 2, 245-253.

* cited by examiner

*Primary Examiner*—Nicholas D Lucchesi
*Assistant Examiner*—Laura A Bouchelle
(74) *Attorney, Agent, or Firm*—Young & Thompson

(57) ABSTRACT

A catheter for injecting a therapeutic or diagnostic agent into an organ, in particular the heart, including a flexible exterior tube having a proximal end and a distal end, inside which a needle is mounted to slide axially between retracted and deployed positions in which a tip of the needle, adapted to be inserted into the organ, is withdrawn inside the exterior tube and projects from the distal end thereof, respectively. Actuation elements are adapted to slide the needle between the retracted and deployed positions. The catheter includes elements for fixing the catheter to the organ, the needle being decoupled from the fixing elements so that the needle is able to slide relative to the fixing elements, at least in an unfolded position of the fixing elements. The fixing elements include a suction cup mounted so that it may be retracted into a lumen of the exterior tube.

14 Claims, 3 Drawing Sheets

DIAGNOSTIC AND INJECTION CATHETER, IN PARTICULAR FOR AN APPLICATION IN CARDIOLOGY

The invention relates to a catheter for locating and/or diagnosing a lesion and/or injecting a therapeutic or diagnostic agent into an organ, in particular into a heart.

To minimize lesions as far as possible, physicians and/or surgeons use "interventional" techniques taking advantage of natural orifices or pathways of the body or make small incisions of a few millimeters at the surface of the body (percutaneous route) in order to introduce devices carrying diagnostic or therapeutic means into the body. Then they guide them to the target organ to be treated. For example, such devices may be endoscopes (thoracoscopes, laparoscopes, arthroscopes) or catheters. For example, the diagnostic or therapeutic means comprise means for injecting an agent adapted to dissolve a thrombus or an anticancer drug, ablation means such as a laser or an ultrasound emitter, associated where applicable with means for aspirating debris, a stent, etc.

These devices may include in particular injection catheters for injecting a treatment agent into an organ located inside the body.

For example, EP 1 205 156 discloses a flexible injection catheter provided with a retractable needle. In addition to the function of injecting a product, the needle also has an electrode function, and therefore enables location of dead or diseased cardiac tissue followed immediately by injection into that tissue of a fluid containing a treatment agent. The needle has both a diagnostic function and a therapeutic function.

Inserting the needle into the wall of the organ is a delicate operation. This operation being carried out remotely, by means of a control handle at the proximal end of the catheter, the needle cannot be pushed in the same way as the needle of a syringe would be. The needle is advanced slowly toward the wall of the organ and there is no beneficial impact effect to assist its insertion therein. The wall of the organ therefore tends to be pushed back by the needle.

Inserting the needle may be even more difficult in the event of local fibrosis, for example following an infarction causing a lesion of the myocardium stiffening the tissue of the wall of the organ.

Finally, after penetration, the needle is not secured in position. If the needle is not pushed in far enough, it may escape, for example because of the retrograde effect of an impact, the ejection of the injected fluid, or a movement of the organ, for example a beat of the heart.

EP 0 980 226 discloses a catheter whose needle is helicoidal. This needle is screwed into the tissue before injection. To position the tip of the needle in the tissue, only slight penetration is necessary, deep penetration resulting from subsequent screwing in of the needle. Furthermore, thanks to the screwing in of the needle, there is no risk of the needle escaping after it has been positioned.

However, the needle must be screwed far enough into the wall of the organ to allow injection at an appropriate depth. This way of fixing the needle therefore has the drawback of locally damaging the wall of the organ in particular if a deep injection or injection into several sites of the tissue is required. If the tissue is dead, the risk of coring, i.e. of ablation of tissue when unscrewing the needle, is not excluded either.

There is therefore a requirement for an injection catheter that facilitates penetration of the needle into an organ and is free of the above drawbacks.

According to the invention, this object is achieved by means of a catheter for injecting a therapeutic or diagnostic agent into an organ, in particular a heart, the catheter comprising:
- a flexible exterior tube having a proximal end and a distal end, inside which a needle is mounted to slide axially between retracted and deployed positions in which a tip of said needle, adapted to be inserted into said organ, is withdrawn inside said exterior tube and projects from said distal end of said exterior tube, respectively,
- actuation means adapted to slide said needle between said retracted and deployed positions, and
- means for fixing said catheter to said organ, mobile between folded and unfolded positions.

The catheter of the invention is noteworthy in that said needle is decoupled from said fixing means so that said needle is able to slide relative to said fixing means, at least in an unfolded position of said fixing means.

Decoupling the needle and the fixing means allows the needle to slide independently of the actuation of the fixing means, at least in the deployed position of the latter.

As will emerge in more detail hereinafter, it is therefore possible to deploy the fixing means, to fix them to the organ, and only then to slide the needle out to perform the injection. Unlike the catheter described in EP 0 980 226, the functions of immobilizing the catheter relative to the organ during penetration of the needle and of adjusting the depth of the tip are no longer related. The immobilization function is provided by the fixing means, which immobilize the catheter relative to the organ, without immobilizing the needle. The depth of the tip in the organ is adjusted in the conventional way by corresponding sliding of the needle in the outer tube. It is therefore advantageously possible to position the tip of the needle at any depth, independently of the fixing means. This has the advantage that if any lesion is caused by the fixing means it is always superficial.

Furthermore, thanks to the fixing means of the invention, movement of the distal end of the catheter, which is fastened to the fixing means, relative to the organ may be eliminated before any penetration of the needle into the organ. Thus the distal end of the catheter is unable to retract because of reaction forces to penetration of the needle into the organ, injection of fluid into the organ or movement of the organ. Penetration of the needle into the organ is facilitated and injection is more reliable.

After fixing, the distal end of the catheter may advantageously move with the surface of the organ to which it is fixed, relative to the physician, without such movements impeding the physician during the injection. The catheter of the invention is therefore particularly suitable for cardiological applications with the heart beating.

Said fixing means preferably comprise a suction cup, commonly called a "sucker", that is preferably mounted so that it may be retracted inside said exterior tube. Using a suction cup has the advantage of avoiding penetration into the wall of the organ and therefore eliminates the possibility of lesion.

The catheter of the invention preferably also has the following preferred features:
- Said fixing means are mobile between folded and unfolded positions with said needle in said retracted position.
- Said catheter comprises an evacuation conduit opening into the interior of said suction cup and adapted to be connected to suction means.
- Said suction cup is mounted so that it may be retracted into a lumen of said exterior tube. The possibility of retracting the suction cup allows intervention that is relatively non invasive, via small orifices and small arteries and/or veins. This feature also facilitates extraction of the catheter on completion of the intervention. Moreover, the retractability of the suction cup enables it to be made larger than would otherwise be the case. It is therefore advantageously possible, after fixing the suction cup to the wall of the organ, to apply a high suction force. This increases the stability of the catheter in this position.

The catheter according to the invention comprises an electrode electrically connected to said needle and/or to said distal end of said exterior tube and/or to said fixing means.

The catheter according to the invention comprises a first electrode electrically connected to said needle and a second electrode of the opposite polarity to that of said first electrode and fixed to said fixing means so as to be able to come into electrical contact with said organ in said unfolded position.

Said first electrode is of negative polarity.

Said second electrode is fixed to a peripheral rim of said suction cup. The option of using a large suction cup, which is made possible because it may be retracted into the exterior tube, advantageously allows the first electrode to be moved far away from the second electrode in the deployed position of the suction cup. This advantageously increases the accuracy of the local measurement of electrical conductivity.

Said second electrode takes the form of a wire extending along said peripheral rim, which may be of positive polarity.

Said needle has a tip with a substantially radial injection orifice.

Said distal end of said exterior tube is provided with an inflatable balloon.

Other features and advantages of the present invention will become apparent on reading the following description and examining the accompanying drawings, in which.

Figure 1:
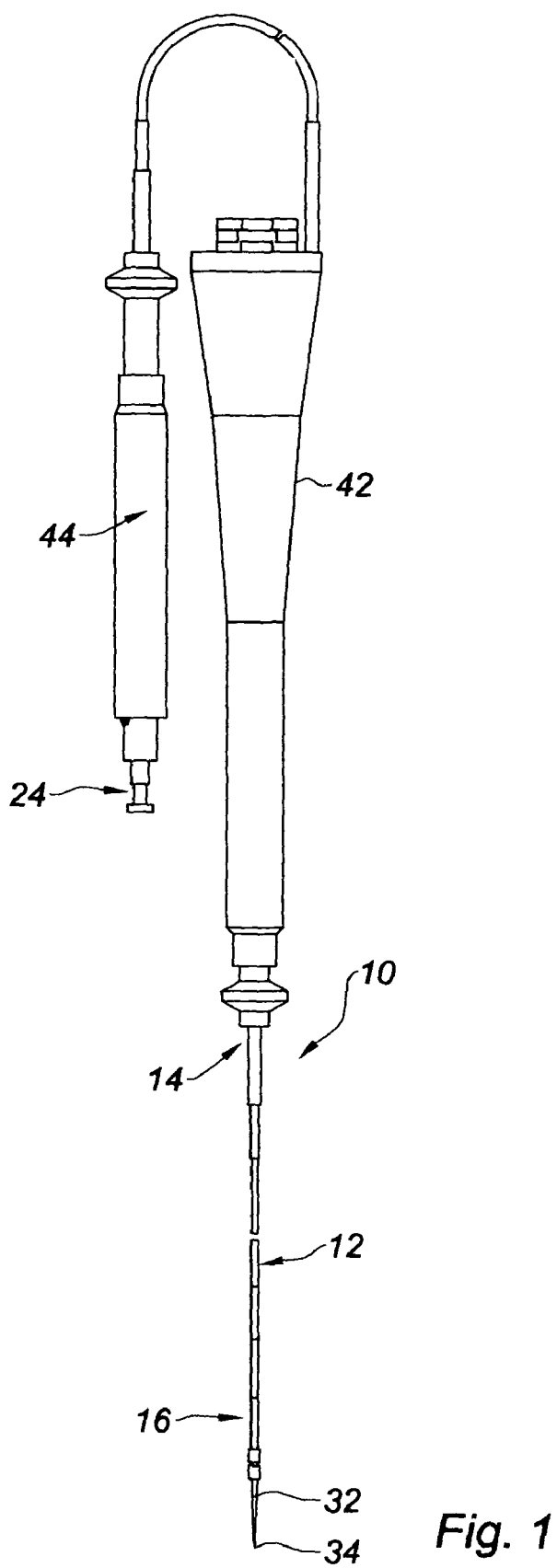
FIG. 1 is a general view of an injection catheter.

In the conventional way, an injection catheter 10 comprises a flexible exterior tube 12 having proximal and distal ends 14 and 16, respectively, with a longitudinal lumen 18 passing through it from the proximal end 14 to the distal end 16.

A tube 22, preferably a central tube, terminating in proximal and distal ends 24 and 26, respectively, is slidably mounted in the lumen 18 of the exterior tube 12. The proximal end 24 of the central tube 22 may be connected to a reservoir containing a fluid to be injected and to means adapted to expel said fluid toward the central tube 22. For example, the proximal end 24 of the central tube 22 may be connected to a syringe, not shown.

The distal end 26 of the central tube 22 is extended by an injection needle 32 having an axis AA and terminating in a tip 34 in which there is an injection opening 36 extending substantially to the end of the tip 34. The needle 32 may be made in one piece with the central tube 22 or fixed coaxially thereto, extending it.

The needle 32 is such that sliding of the central tube 22 in the exterior tube 12 causes movement of the tip 34 between retracted and deployed positions. In the retracted position, the tip 34 is inside the exterior tube 12, in the lumen 18. In particular, the retracted position facilitates the introduction of the catheter 10 into the body and its guidance to the injection site on the organ to be treated or investigated.

In the deployed position, the needle 32 projects out of the distal end 16 of the exterior tube 12 and may therefore be inserted at the injection site.

In the conventional way, the proximal end 14 of the exterior tube 12 of the catheter 10 comprises a control handle 42 for controlling the needle 32, causing the central tube 22 and the needle 32 to move in the exterior tube 12. As will emerge in more detail hereinafter, the handle 42 is used in particular to cause the tip 34 of the needle 32 to project out of the exterior tube 12 in the vicinity of the injection site and then to push it into the tissue of the organ into which fluid must be injected.

The catheter 10 also includes a handle 44 for controlling the position of the distal end 16 of the exterior tube 12, enabling the user to bend the distal end 16. The catheter may finally comprise location means, not shown, for example using ultrasound scanning.

The catheter is preferably fabricated from materials compatible with nuclear magnetic resonance (NMR).

According to the invention, the catheter 10 further comprises means 50 for fixing the catheter to a wall P of an organ O to be treated or diagnosed.

The fixing means may comprise one or more claws, for example, a suction cup or a screw.

The fixing means preferably comprise a plurality of attachment points disposed at regular intervals around the exterior tube 12. For example, the catheter 10 may comprise three claws at 120° to each other around the exterior tube 12.

Figure 2:
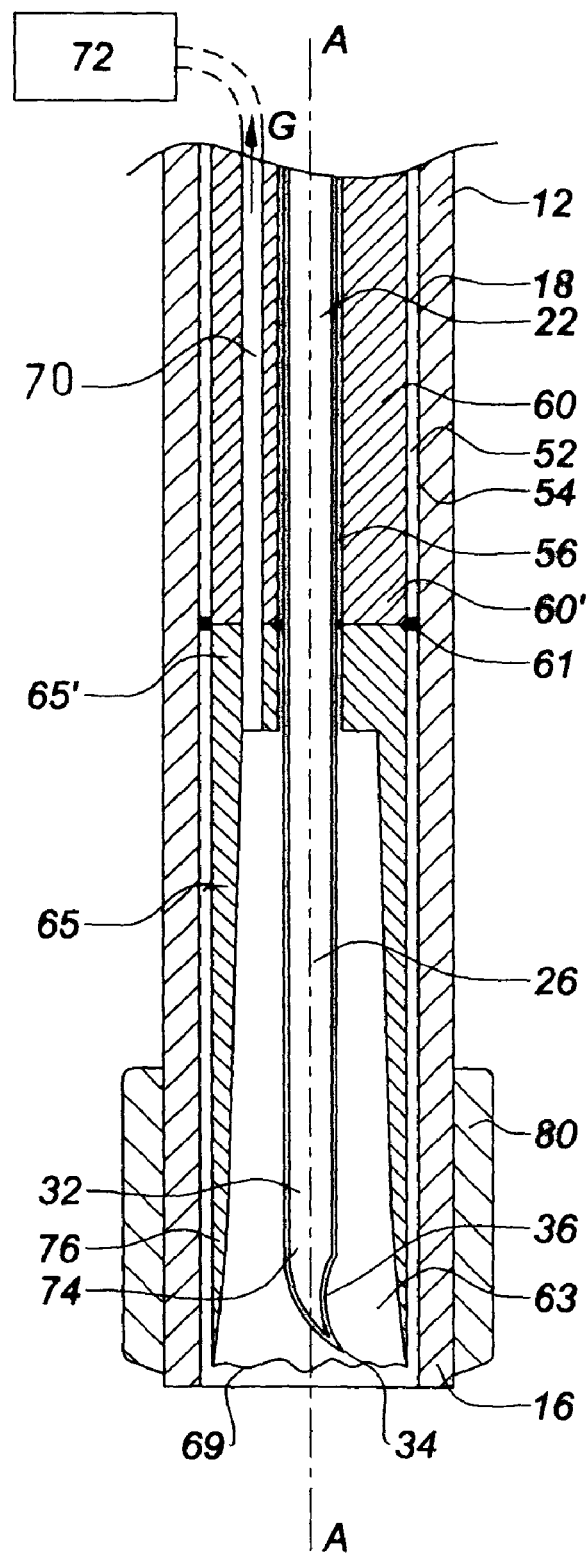
FIGS. 2 and 3 are diagrammatic views in longitudinal section of the distal end of a catheter of the invention, with the fixing means in folded and unfolded positions, respectively, and the needle of the catheter in retracted and deployed positions, respectively.
Figure 3:
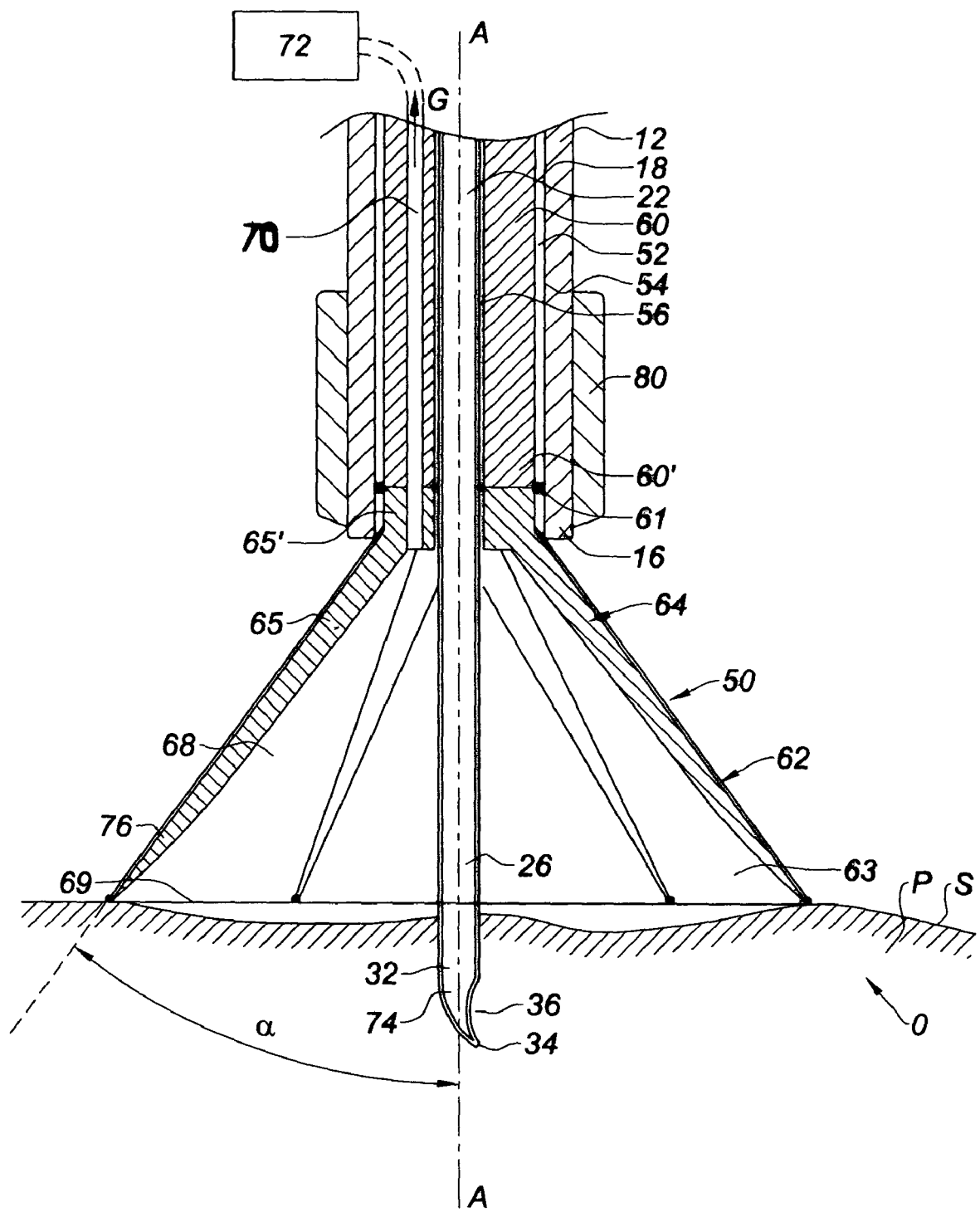

The fixing means 50 are mobile between a folded position (FIG. 2) and an unfolded position (FIG. 3).

In the folded, or "stowed" position, the fixing means 50 are retracted at least partly, and preferably totally, into the lumen 18 of the exterior tube 12, preferably in an annular space 52 separating an interior surface 54 of the exterior tube 12 and an exterior surface 56 of said needle 32 or of said central tube 22.

The folded position facilitates guiding the distal end 16 of the exterior tube 12 inside the body, between the exterior of the body and the injection site, all risk of unintentional snagging of the tip 34 on organs of the body being eliminated.

In the unfolded position, the fixing means 50 are at least in part "deployed", i.e. extended out of the exterior tube 12, so that they may be fixed to an exterior surface S of the organ O to be treated.

The fixing means 50 may be moved between the folded and unfolded positions remotely, from outside the body, using actuation means. The actuation means may comprise, for example, a sleeve or "sheath" 60 slidably mounted in the annular space 52, whose distal end 60' is fastened to the fixing means and whose proximal end may be manipulated by the physician, for example by means of the control handle 42, which is appropriately adapted for this purpose.

The fixing means 50 are adapted to slide axially in the annular space 52, sealing means 61 being provided between the fixing means, on the one hand, and the exterior tube 12 and the central tube 22, on the other hand.

The actuation means are preferably conformed to allow the physician to operate the fixing means 50 independently of axial movement of the needle 32.

The fixing means 50 preferably comprise at least one suction cup 62 that, preferably, is retractable into the annular space 52 and has the needle 32 or the central tube 22 passing axially through it. The suction cup 62 is preferably conformed to deploy of its own accord on leaving the annular space 52.

The suction cup 62 preferably comprises a web 63 fixed to a frame 64. The web 63 is preferably made of a flexible material, for example polytetrafluoroethylene (PTFE), polyethylene teraphthalate (PETP), silicone, or preferably polyurethane. The web 62 is preferably made of an elastic material encouraging its deployment.

The frame 64 comprises a plurality of flexible rods 65 fixed at an inner end 65' to the distal end 60' of the sleeve 60 and substantially equi-angularly disposed around the axis AA of the needle. The rods 65 are fixed to the web 63 like the ribs of an umbrella to tension and stiffen the web 63 in the unfolded position of the suction cup 62.

The rods 65, which are made of stainless steel, for example, may be rotatably mounted at the distal end 60' of the sleeve 60 about respective tangential axes between the folded position in which the rods 65 are substantially aligned with the axis AA of the needle (FIG. 2) and the unfolded position in which they form with that axis an angle α (FIG. 3). The unfolding of the rods is preferably limited so that they are not able to form with the axis AA of the needle an angle α greater than 60°. This has the advantage of guaranteeing easy folding of the suction cup. The unfolding of the frame 64 is limited by the tension of the web 63 in the unfolded position and/or by a stop on the sleeve 60 preventing total extraction of the rods 65 from the annular space 52. It is preferable if redundant means are used to limit unfolding in order to protect against failure of one of them, for example tearing of the web 63.

The maximum angle α is preferably from 30° to 60° and more preferably equal to approximately 45°.

The rods 65 are preferably made from a shape memory material, preferably nitinol, and conformed so as to deform of their own accord from the folded position to the unfolded position after their extraction from the annular space 52, and the interior ends 65' are preferably fixed rigidly to the distal end 60' of the sleeve 60.

In the unfolded position (see FIG. 3), the web 63 assumes the shape of a cone or a dome, defining an interior volume 68 under the suction cup 62. The base of said cone is delimited by a peripheral rim 69.

An evacuation conduit 70 preferably passes through the web 63 and is connected to suction or "vacuum" means 72 adapted to reduce the pressure in said interior volume 68 and then to maintain the reduced pressure. The evacuation conduit 70 may advantageously be formed at least in part within the thickness of the wall of the sleeve 60.

The suction means 72 are preferably disposed in the vicinity of the proximal end 14 of the catheter 10. The centralized vacuum system usually available in hospitals may be used as the suction means 72. To clarify the drawing, the suction means are shown only in FIG. 3.

The catheter 10 of the invention preferably comprises, in the vicinity of the distal end 16 of the exterior tube 12, at least one electrode 74 connected to control or diagnostic means, not shown, adapted to measure the local conductivity of the organ O and to determine therefrom the condition of the tissue of the organ O in contact with the electrode 74.

The electrode 74 may be electrically connected to an electrically conductive portion of the distal end 16 of the exterior tube 12, for example to a metal ring around the distal end 16 of the exterior tube 12.

The needle 32 is preferably made from an electrically conductive material and constitutes the end of the electrode 74. The electrode 74 is preferably carried by or incorporates the central tube 22 and/or the needle 32, as in this embodiment of the invention.

To effect a measurement by means of an electrode 74 in the form of a needle, it is nevertheless necessary to penetrate the organ O, even slightly, which is not always desirable. In one variant of the invention, an electrode is electrically connected to an electrically conductive portion 76 of the fixing means, for example to a metal rod 65 extending as far as the peripheral rim 69 of the suction cup 62 so as to come into contact with the surface S. A plurality of tubes 65 that are not electrically interconnected and are equi-angularly disposed relative to each other preferably serve as electrodes. This has the advantage of making the measurement more accurate.

The catheter of the invention preferably comprises a first electrode electrically connected to the needle 32 and a second electrode, of opposite polarity to the first electrode, fixed to the fixing means so as to be able to come into electrical contact with the surface S of the organ O in the unfolded position. The second electrode comprises one or more rods 65, for example, where applicable connected to an electrically conductive wire extending along the peripheral rim 69 of the suction cup 62 and preferably in the form of a ring.

Using two electrodes has the advantage of enabling accurate local measurement of electrical conductivity.

The first electrode is preferably of negative polarity and the second electrode of positive polarity.

The tip 34 of the needle 32 is conventionally provided with at least one injection opening 36 through which fluid may be expelled from the central tube 22. The injection opening 36 is preferably oriented substantially radially. Because the fluid to be injected is then evacuated substantially radially from the needle 32, the reaction force on the needle 32 resulting from the ejection of the fluid, and tending to move the needle 32 axially away from the tissue into which it has penetrated, is advantageously reduced. This facilitates its retention in position by the fixing means, which may therefore be more compact.

This advantageously eliminates the risk of coring by the needle 32 and even of perforation of the wall P of the organ O.

An inflatable balloon 80 is preferably disposed at the distal end 16 of the exterior tube 12 and adapted to be selectively inflated and deflated from outside the body, for example by means of a pump, not shown.

The catheter 10 of the invention operates in the following manner:

To treat an organ O of a human or animal body, for example to diagnose dead areas of a heart and inject a therapeutic agent into those areas, the physician may proceed as follows:

Initially, the physician makes a mini-incision or puncture at an appropriate place on the body and then inserts the distal end 16 of the catheter 10 of the invention into mini-incision and guides it to the heart via a vascular route, with the aid of information provided by the location means.

The balloon 80 may be inflated continuously or intermittently during this process. Inflating the balloon 80 advantageously enables improved location of the distal end 16 of the catheter 10 using ultrasound equipment, a technique of low cost compared to the mapping equipment usually employed.

When the catheter 10 is fed through a blood vessel, inflating the balloon 80 may also facilitate entrainment of the balloon 80 by the blood flow.

The physician then manipulates the catheter 10 to bring the needle/electrode 32 of the catheter 10 into contact with the wall P of the heart, without causing it to penetrate deep into the heart. This operation is referred to hereinafter as a "diagnostic needle insertion". At this stage the needle 32 serves as an electrode for measuring the local electrical conductivity of the tissue with which it is in contact. This measurement is interpreted by diagnostic means which evaluate the condition of the tissue.

According to the invention, if the organ O is a human heart, the measurements of the local electrical conductivity of the tissue are used to determine the potential activity of the myocardium and in this case the measured electrical conductivity is referred to as the "myocardial depolarization signal".

According to the invention, a myocardial infarction is considered to be diagnosed if the following two conditions are satisfied simultaneously:

An endocavity ventricular electrogram depolarization slew rate of less than 0.5 volts per second.

An endocavity ventricular electrogram amplitude of less than 5 millivolts, which constitutes a "microvoltage".

Thus the needle 32 contributes to establishing a diagnosis of the tissue with which it is in contact. It is therefore easier for the physician to position the needle 32 correctly before the injection.

In the event of a diagnosis justifying an injection of therapeutic agent, called a "positive diagnosis", for example in the event of a positive diagnosis of myocardial infarction, the injection may advantageously be effected immediately, possibly after pushing the needle 32 a little further into the organ O, but without having to renew the needle insertion. The lesions occasioned are therefore minimal.

Moreover, the injection point advantageously coincides with the point of the diagnostic needle insertion and is therefore perfectly superposed on the site where the positive diagnosis was made.

Finally, an injection carried out immediately after a diagnosis provides for very rapid execution of the procedure.

According to the invention, before the injection, the suction cup 62 around the needle 32 is deployed out of the annular space 52 to assume the unfolded position. To this end, the physician slides the sleeve 60 in the annular space 52 in such a way as to push the frame 64 out of the annular space 52.

On leaving the distal end of the exterior tube 12, the suction cup 62 is deployed to the unfolded position by its inherent elasticity and/or deformation of the rods 65.

The physician then brings the peripheral rim 69 of the suction cup 62 into contact with the surface S of the organ O.

The fixing of the suction cup 62 to the wall P of the organ O results from a reduction of the pressure in the interior volume 68 through evacuation of material by the suction means 72 via the evacuation conduit 70 (arrow G).

After the suction cup 62 is fixed, the distal end 16 of the catheter is immobilized in position relative to the organ O by maintaining a predetermined reduced pressure in the interior volume 68. If the seal at the contact between the peripheral rim 69 of the suction cup 62 and the surface S of the wall P is not perfect, maintaining the reduced pressure necessitates regulation of the suction means 72, the reduced pressure preferably being monitored by means of a pressure gauge.

According to the invention, immobilizing the distal end 16 of the catheter relative to the organ O does not impede the sliding of the needle 32 along its axis AA. The physician may therefore inject the agent immediately without risk of accidental detachment of the needle 32.

To reach greater depths, the physician may if necessary push the needle 32 further into the organ O, with no risk of the needle becoming detached.

On completion of the injection, the physician retracts the needle 32. Leaving the suction cup 62 in position advantageously enables it to prevent tearing on retraction of the needle 32 into the lumen 18 of the exterior tube 12. This feature is particularly advantageous when operating on a heart that is still beating.

The physician then releases the suction cup 62 by releasing the depression in the interior volume 68, for example by turning off the suction means 72. He then stows the suction cup 62 in the annular space 52, in the folded position, by pulling the sleeve 60 toward the proximal end of the catheter.

The physician may then guide the distal end 16 of the catheter 10 to the next site to be diagnosed.

In a variant of the invention, the suction cup 62 may be fixed before carrying out each diagnostic needle insertion. This has the advantage of facilitating the needle/electrode insertion.

The suction cup 62 and the needle 32 are preferably retracted into the exterior tube 12 during the movement between one diagnostic needle insertion and the next, and then deployed immediately before carrying out the next needle insertion.

The deployment of the suction cup 62 is preferably independent of that of the needle 32. The suction cup 62 is preferably deployed and fixed to the organ O with the needle 32 retained in the retracted position.

Of course, the present invention is not limited to the embodiment described and shown by way of illustrative and nonlimiting example.

For example, to facilitate the manipulations required of the physician, the deployment of the suction cup 62 could be caused by the deployment of the needle 32. In this case, it is preferable if the deployment of the suction cup 62 precedes the deployment of the needle 32 sufficiently to prevent the tip of the needle 32 projecting from the surface defined by the peripheral rim 69, at least until the unfolded position of the suction cup 62 is reached.

The fluid injected may be any therapeutic or diagnostic agent, for example cells, genes, medication, contrast agents, growth factors, etc.

The actuation means are not limited to the means described. In particular, hydraulic actuation means may be envisaged.

The means actuating sliding of the needle may be manual or electronic.

The invention claimed is:

1. Catheter for injecting a therapeutic or diagnostic agent into an organ (0), in particular a heart, the catheter comprising:
    a flexible exterior tube (12) having a proximal end (14) and a distal end (16), inside which a needle (32) is mounted to slide axially between retracted and deployed positions in which a tip (34) of said needle (32), adapted to be inserted into said organ (O), is withdrawn inside said exterior tube (12) and projects from said distal end (16) of said exterior tube (12), respectively,
    actuation means adapted to slide said needle (32) between said retracted and deployed positions, and
    means (50) for fixing said catheter to said organ (0), said needle (32) being decoupled from said fixing means so that said needle (32) is able to slide relative to said fixing means, at least in an unfolded position of said fixing means (50), which catheter is characterized in that said fixing means (50) comprise a suction cup (62) mounted so that it may be retracted into a lumen (18) of said exterior tube (12).

2. Catheter according to claim 1, characterized in that said fixing means (50) are mobile between folded and unfolded positions with said needle (32) in said retracted position.

3. Catheter according to claim 2, characterized in that it comprises an evacuation conduit (70) opening into the interior of said suction cup (62) and adapted to be connected to suction means (72).

4. Catheter according to claim 1, characterized in that it comprises an evacuation conduit (70) opening into the interior of said suction cup (62) and adapted to be connected to suction means (72).

5. Catheter according to claim 1, characterized in that it comprises an electrode(74)electrically connected to said needle (32) and/or to said distal end (16) of said exterior tube (12) and /or to said fixing means (50).

6. Catheter according to claim 1, characterized in that it comprises a first electrode (74) electrically connected to said needle (32) and a second electrode of the opposite polarity to that of said first electrode (74) and fixed to said fixing means (50) so as to be able to come into electrical contact with said organ (O) in said unfolded position.

7. Catheter according to claim 6, characterized in that said first electrode (74) is of negative polarity.

8. Catheter according to claim 7, characterized in that said second electrode is fixed to a peripheral rim (69) of said suction cup (62).

9. Catheter according to claim 8, characterized in that said second electrode takes the form of a wire extending along said peripheral rim (69).

10. Catheter according to claim 1, characterized in that said needle (32) has a tip (34) with a substantially radial injection orifice (36).

11. Catheter according to claim 1, characterized in that said distal end (16) of said exterior tube (12) is provided with an inflatable balloon (80).

12. A catheter for injecting a therapeutic or diagnostic agent into an organ, the catheter comprising:

a flexible exterior tube having proximal and distal ends;

a needle adapted to be inserted into an organ and that is axially movable inside said tube between retracted and deployed positions in which a tip of said needle is withdrawn inside said distal end of said tube and projects from said distal end of said tube, respectively;

a first actuator that moves said needle between the retracted and deployed positions; and a suction cup adapted to fix the catheter to an organ and that is axially movable inside said tube between withdrawn and projected positions in which said suction cup is withdrawn inside said distal end of said tube and projects from said distal end of said tube, respectively, said needle being decoupled from said suction cup so that said needle moves relative to said suction cup when said suction cup is in the projected position.

13. The catheter of claim 12, further comprising a second actuator, separate from said first actuator, that moves said suction cup between the withdrawn and projected positions.

14. The catheter of claim 13, wherein said second actuator comprises an annular sheath slidably mounted between an interior surface of said exterior tube and an exterior surface of said needle.

* * * * *